United States Patent [19]

Man

[11] Patent Number: Plant 7,043

[45] Date of Patent: Oct. 3, 1989

[54] DISTINCT VARIETY OF BEGONIA PLANT NAMED SONATA

[75] Inventor: Jan Man, Lisse, Netherlands

[73] Assignee: Oglevee Ltd., Connellsville, Pa.

[21] Appl. No.: 251,686

[22] Filed: Sep. 29, 1988

[51] Int. Cl.[4] ..... A01H 5/00

[52] U.S. Cl. ..... Plt./68

[58] Field of Search ..... Plt. 68

*Primary Examiner*—James R. Feyrer

*Attorney, Agent, or Firm*—Webb, Burden, Ziesenheim & Webb

[57] ABSTRACT

A new Begonia variety is characterized by its vigorous growth and flowering. The plant is highly floriferous and the entire plant becomes covered with bloom. The new cultivar is long lasting and has a visually pleasing contrast between the creamy white flower and the dark foliage.

1 Drawing Sheet

BACKGROUND OF THE NEW PLANT

The present invention comprises a new and distinct cultivar of *Begonia*×*hiemalis* known by the varietal name of Sonata. The new cultivar is a selection of a selfing of the cultivar Petra (U.S. Plant Pat. No. 6,321). The new cultivar is a double white seedling of Petra with smaller and lighter color leaves. The plant is also taller than Petra.

The new cultivar was discovered in March of 1985 at Limaplant b.v. in Lisse, Holland; was first asexually reproduced by cuttings at Limaplant b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by its long lasting abundant floriferousness, vigorous growth and flowering. The appearance is very pleasing with a strong contrast between the creamy white flowers against the dark green foliage.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 62° F. at night and 68° F. during the day. The plants were potted in July of 1987 in a peat-lite mix and fertilized with a mixture of 20N-10P-20K. Color readings were taken indoors under 200 footcandles of cool white fluorescent tubes. Color references are to The R.H.S. Colour Chart of The Royal Horticultural Society of London, unless noted differently.

Botanical classification: *Begonia*×*hiemalis.*

Flower:

*Fully expanded.*—3.5 to 4.0 cm. in diameter; side view: flattened oval in appearance.

*Buds.*—2 cm. wide; lower ½: yellow-green group 145D; upper ½: red group 49C; edge: red group 49A. Color shift is gradual with no lines of division.

*Borne.*—Compound dichasium with opposite bracts at the base of each flower cluster.

*Bracts.*—Are characterized by an obtuse base with a slightly undulate margin and occur on bifurcation of the inflorescence.

*Stems.*—Peduncles are strong and upright; main peduncle 6 mm. in diameter; color yellow-green group 145B.

Form.—Double. Each flower generally has 2 sepals and 12 to 15 petals and petaloids.

*Permanence.*—Very long lasting bloom with average life span of 3 weeks.

Color:

*Tonality from a distance.*—The basic hue is a creamy white, the open mature flower has very light shades of yellow in the petals with a light green center.

*Front of petals.*—Fully mature and expanded and are characterized by the color white group 155A.

*Reverse of petals.*—Fully mature and expanded and are characterized by the color white group 155A.

*Base of petals.*—Yellow group 4C. Calyx: Front of calyx — White group 155A. Reverse of calyx — White group 155A for a fully open flower. When the calyx appears to enclose the whole flower in the early stages of development, its reverse is a light green. Bract — Color yellow green group 145C.

*Throat.*—None.

*Discoloration.*—None.

Petals:

*Texture.*—Crepe paper like (gentle crinkles).

*Appearance.*—Oval with yellow attachment.

*Arrangement.*—Semi-double.

*Persistence.*—Very good flowering response, produces a very large number of flower buds.

*Fragrance.*—None observed.

Reproductive organs: All reproductive organs have modified into petaloids. Anthers, filament, pollen, style and ovaries could not be observed.

Plant:

*Form.*—Short, compact internodes 2 to 3 cm apart; upright; excellent basal branching; strong stems provide good self-support strength.

*Growth.*—Very vigorous; excellent for production scheduling.

*Height from soil line.*—18 to 20 cm. in 11 weeks (no pinch, no cycocel).

*Spread.*—26 to 28 cm. in 11 weeks (no pinch, no cycocel).

Foliage:

*Size.*—Average length is 12 cm. and average width of 6 cm. on a leaf 5 nodes below the terminal bud.

*Quantity.*—Due to short internodes, there are many leaves.

*Shape.*—Acute tip with irregularly lobed attachment; edge is slightly doubly serrate.

*Top side.*—Green group 137B; shiny and smooth.

*Underside.*—Green group 138C with shades of red between the hues.

*Ribs and veins.*—Smooth on top side, raised on lower side, lower side veins only area on leaf where visible tricomes (hairs) appear.

*Rib and vein color.*—Top side: yellow-green group 144B, bottom side: yellow-green group 146D.

*Margin.*—None.

*Stipules.*—None.

I claim:

1. A new and distinct variety of Begonia characterized by long lasting and abundant floriferousness, vigorous growth and flowering, contrast between creamy white flower and dark foliage as herein shown and described.

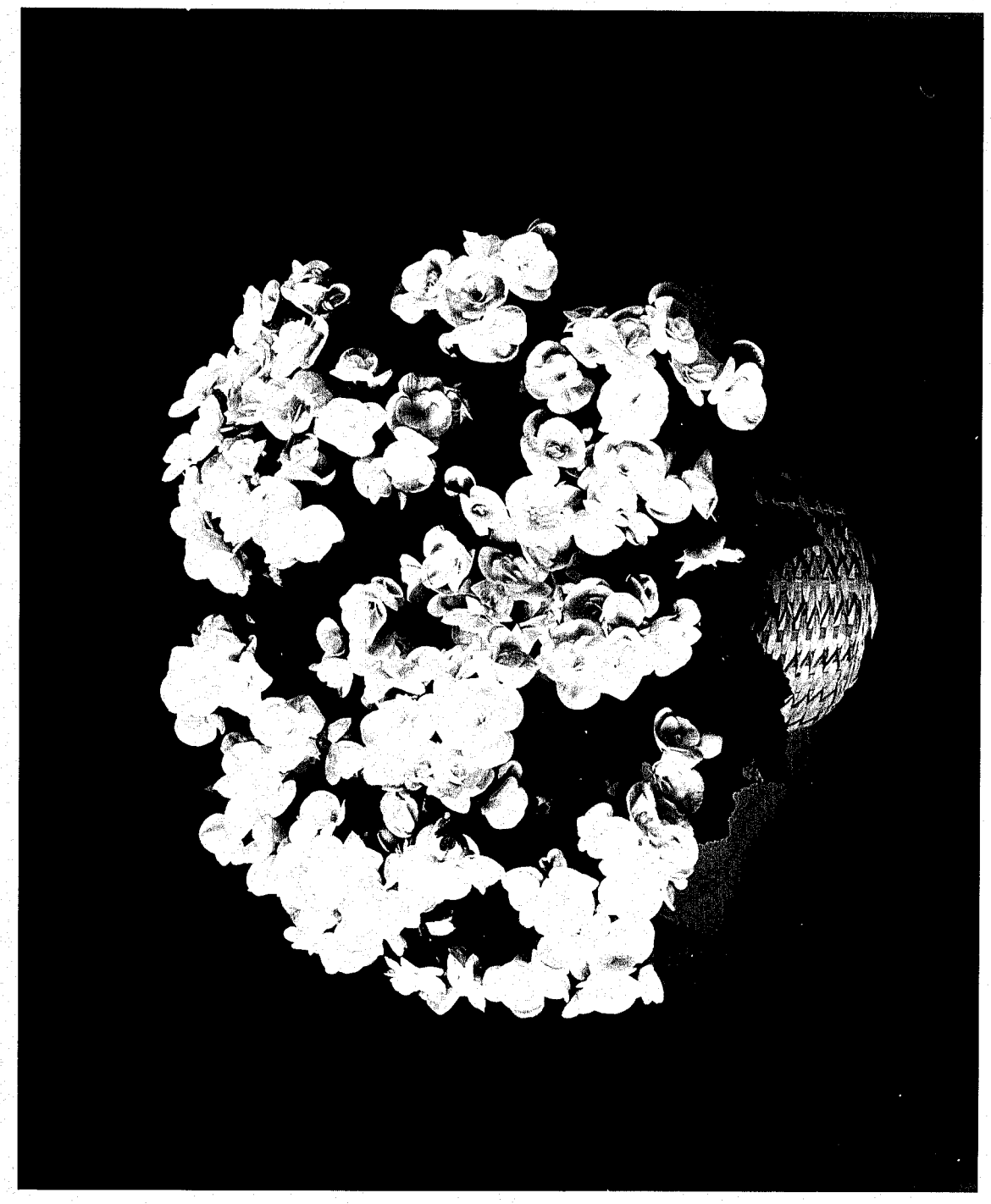

* * * * *